(12) United States Patent
Golombek et al.

(10) Patent No.: US 8,195,404 B2
(45) Date of Patent: Jun. 5, 2012

(54) SMALL ORGANISM LOCOMOTOR RECORDING PROCEDURE AND DEVICE, BEHAVIORAL RECORD OBTAINED AND USE OF SAME

(75) Inventors: Diego Andres Golombek, Buenos Aires (AR); Sergio Hernan Simonetta, Lomas de Zamora (AR)

(73) Assignees: Consejo Nacional De Investigaciones Cientificas Y Techicas (CONICET), Buenos Aires (AR); Universidad Nacional De Quilmes, Bernal (AR); Inis Biotech LLC, Milford, DE (US)

( * ) Notice: Subject to any disclaimer, the term of this patent is extended or adjusted under 35 U.S.C. 154(b) by 534 days.

(21) Appl. No.: 12/515,723

(22) PCT Filed: Nov. 14, 2007

(86) PCT No.: PCT/IB2007/054628
§ 371 (c)(1),
(2), (4) Date: Jul. 2, 2009

(87) PCT Pub. No.: WO2008/062347
PCT Pub. Date: May 29, 2008

(65) Prior Publication Data
US 2010/0063744 A1    Mar. 11, 2010

(30) Foreign Application Priority Data
Nov. 21, 2006 (AR) .............. P20060105084

(51) Int. Cl.
*G06F 19/00* (2006.01)
(52) U.S. Cl. .............. 702/19; 702/28; 702/29; 600/476; 600/595; 356/51; 356/432
(58) Field of Classification Search .................... 702/19, 702/28–29; 600/595, 476; 356/432, 51
See application file for complete search history.

(56) References Cited

U.S. PATENT DOCUMENTS

| | | | |
|---|---|---|---|
| 4,896,967 | A | 1/1990 | Douglas-Hamilton et al. |
| 4,917,117 | A | 4/1990 | Brom et al. |
| 5,915,332 | A | 6/1999 | Young et al. |

FOREIGN PATENT DOCUMENTS

| | | |
|---|---|---|
| EP | 0 263 062 | 4/1998 |
| WO | 99/42557 | 8/1999 |

OTHER PUBLICATIONS

International Search Report—PCT/IB2007/054628—Apr. 16, 2008.

*Primary Examiner* — Drew A Dunn
*Assistant Examiner* — Hien Vo
(74) *Attorney, Agent, or Firm* — Young & Thompson

(57) ABSTRACT

The system records the movement of tiny organisms housed in closed micro plates traversed by an infrared beam generating a signal as a function of the diffraction caused by the body of the microorganism. The behavior detection procedure includes processing the diffraction signal to discriminate the locomotor activity of the microorganism. The system may be used in the chronobiological field, longevity, toxicity, and pharmacology studies.

21 Claims, 6 Drawing Sheets

FIG. 5

SMALL ORGANISM LOCOMOTOR RECORDING PROCEDURE AND DEVICE, BEHAVIORAL RECORD OBTAINED AND USE OF SAME

TECHNICAL FIELD

Automation of the behavioral record in model organisms is an extremely useful tool and may be used in the chronobiological field, longevity, toxicity and pharmacology studies. Development of behavioral recording automatic systems allows certain research fields to grow vigorously in a very short time.

The present invention relates to a process and device for locomotor recording of small organisms. Potentially, the invention may be used in developing drugs (i.e. targets or pharmacological objects) and toxins, as well as in locomotion defect, circadian and longevity (or aging) studies, and genetic and mutant screenings.

BACKGROUND ART

Locomotor studies in small organisms are usually performed through indirect measurements (reporter genes) or video recording (bug trackers).

The commercialization of the *Drosophila melonagaster* activity monitoring system (Trikinetics www.trikinetics.com) caused a big impact on research of this animal model. The main characteristic of this equipment is the possibility of recording the activity of a large number of animals, with single animal tracking. This equipment is used in chronobiology and in pharmacological studies involving research from many areas such as Parkinson disease, aging, and toxicity.

However, behavioral studies in smaller organisms have been limited to population measurements or the indirect recording of reporter gene activity. For example, bioluminiscent reporters have been used in cianobacteria; whole population measurements of oxygen consumption and metabolic production or biomass growth have been used for yeast; impedance and optical density of the medium have been employed for bacteria.

Other model organisms, such as zebrafish larvae or the *C. elegans* nematode, have been studied through reporter genes (bioluminisense and biofluorescence) and through video tracking (using video recording plus digital image analysis).

At the moment, complex movement analysis is only possible using 'bug trackers'. However, the implementation of this setup for multiple channel tracking (high number of isolated animals) is not practical. The elevated cost of CCDs and optical equipment, plus the huge amount of data processing required (equivalent to one camera coupled to one microscope, plus one PC per camera) makes it difficult and expensive to use for multi-isolated-organism tracking.

The study of simpler behaviors, such as the possibility to know if an animal moves in one particular moment or even if it is alive, requires simplified systems with the possibility to track multiple individuals simultaneously and real time data processing.

The locomotor system designed for Drosophila and similarly sized insects (*Drosophila* size=5 mm long×3 mm wide, opaque colour) is not suitable for smaller animals. When we attempted to use this system for smaller organisms (i.e. *C. elegans*, about 1 mm long×100 um diameter, translucid) we found many limitations. To name a few: inappropriate culture recipient format (glass tubes of 5 mm diameter), big size of the infrared beam relative to the small organism body (beam=3-5 mm diameter vs. organism=100 um) and lower than required detection sensibility (since flies are not transparent).

SUMMARY OF THE INVENTION

The purpose of the invention is the development of a locomotion activity tracking system for small organisms (with low cost, easy construction and implementation). One particular objective is the implementation to track circadian rhythms and general locomotion in the nematode *C. elegans*.

The present invention concerns an automatic locomotor activity tracking system for very small organisms acting through an infrared microbeam. The procedure of detection is achieved by crossing the organism container (where the organism is cultured) with an infrared microbeam, and generating a signal as a function of the light scattering generated by the diffraction of the organism body. The signal is digitally processed to detect the organism's locomotor activity.

This easy construction and multiple channels system has multiple applications, including those in chronobiology, lifespan, locomotor behavior, toxicology and pharmacology studies.

DESCRIPTION OF DRAWINGS

These and other features and details of the object of this invention and the way the invention may be developed and embodied shall be better understood by the following detailed description of an exemplary and non-limiting embodiment as illustrated in the attached drawings. Notwithstanding other variations, modifications, adaptations and/or additions may be eventually made without altering the nature or departing from the spirit of the invention. In the drawings:

FIG. 5: Data presentation (by actograms) on the screen of the same computer or other computer connected to the network.

DEFINITIONS

V/F=voltage to frequency, LD=light dark cycle, well=microtiter plate container unit.

DISCLOSURE OF INVENTION

Disclosure

The following description shows an application of the invention. An example of application regarding tracking locomotor activity of *C. elegans* is given below. This application is also valid for similarly sized organisms, with the obvious adjustments of culture conditions.

In order to record the movement of individual worms, they are placed in a 96-wells microtiter plate [3] (1 worm per well) (microtiter plate: 'Orange' trademark or similar. The size of this plate is 127 mm long×85 mm wide, and each well size is 7 mm diameter×14 mm deep, with flat or U bottom shape). In the case of nematodes, the best sensitivity is obtained employing U shape microtiter plates (where gravity limits the worm movement area). However, it could be possible to employ flat bottom plates in other population studies (such as fish larvae or insects). In addition, other microtiter plates might be used (12-1536 wells/plate), as long as there is at least 1 microbeam per well in order to track individual animals.

Each microtiter well [3] defines a closed habitat, comprised by the culture medium (in this application we used liquid buffer M9, CeMM (CeHR) or Leivobitz's L15 medium, with low infrared optical absorbance). The culture medium could be axenic or not, and could comprise liquid medium or even air (for insects). The main characteristic to fulfill is the low absorbance in the microbeam wavelength range.

Figure 1:
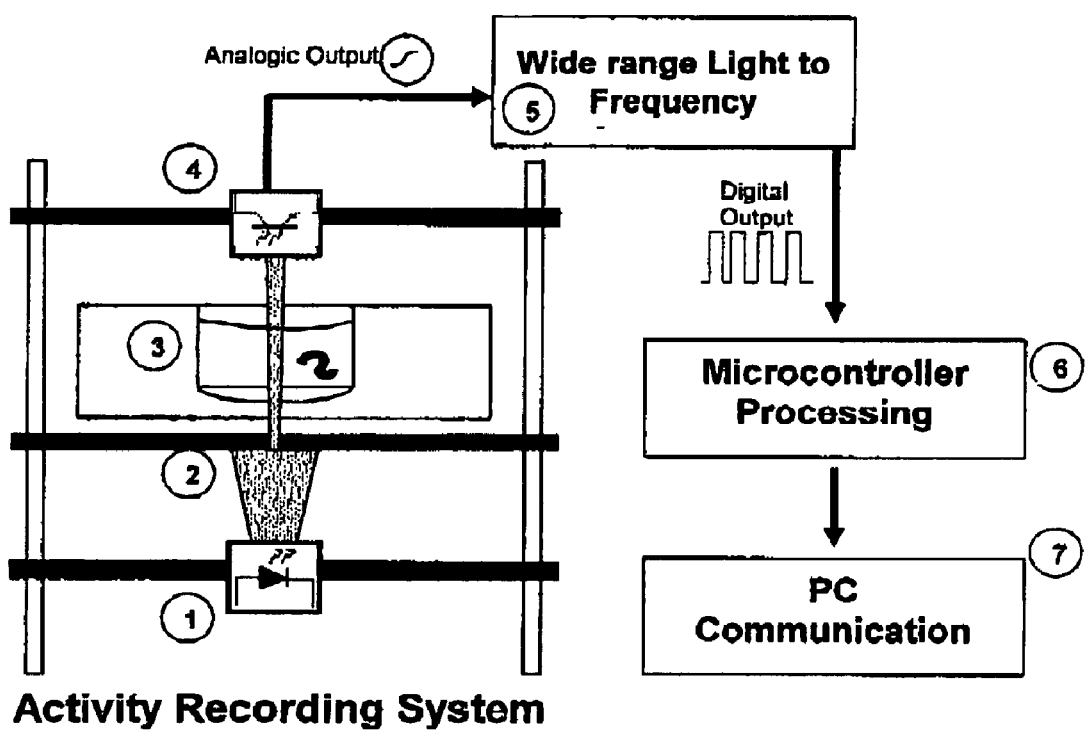
FIG. 1: Schematic diagram of the acquisition system according to the present invention.

The block diagram of the system corresponding to a single well is shown in FIG. 1. The microtiter plate [3] is introduced in the register receptacle, in between an infrared led [1] and a phototransistor [4]. It is suitable to use an infrared beam of wavelength 940 nm with an emission power of 1 mW/cm2 or lower (an example of emitter would be the LED TLN105A Toshiba Semiconductor or similar, and a phototransistor SFH300FA Siemens Semiconductor with ambient light filter or similar). However, the microbeam light might be of any wavelength as long as it does not interfere with the process that is being recorded.

Movement transduction starts with the LED infrared light emission [1]. An infrared microbeam is generated filtering the light by means of a microhole array system [2]. This microbeam crosses the worm culture medium and is received by the phototransistor [4].

The microhole array system is comprised of an acrylic plate (2.5 mm wide) with 100 um microholes aligned with the LEDs. The precise alignment of LEDs, microholes, and phototransistors is obtained using a laser plot system and assembling the setup with guiding screws plus bushings.

Figure 2:
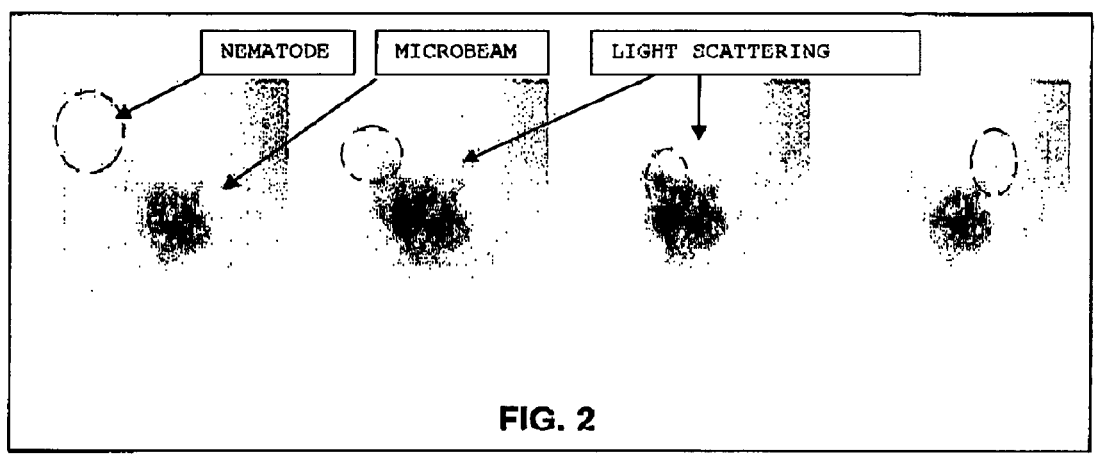
FIG. 2: Video recording of the light scattering produced by the nematode movement.
Figure 3:
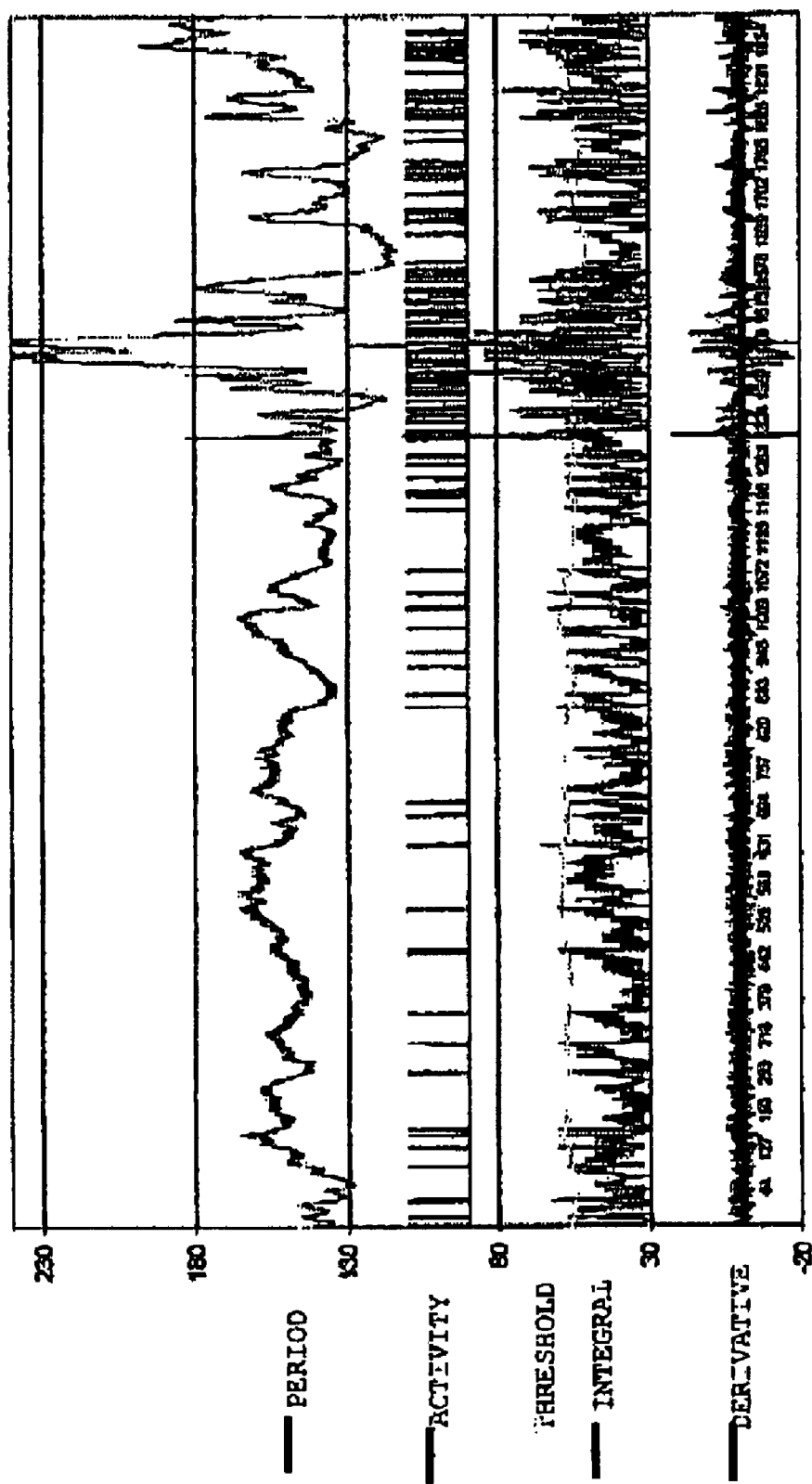
FIG. 3: Plot of the digitally processed signal. a) period of the frequency signal acquired from the V/F converter. b) signal derivative c) integration of derivatives d) threshold e) detected locomotor activity events.

Detection of movement occurs when the worm passes through the infrared microbeam (FIG. 2). As the worm's body scatters the infrared light, it produces a small transient decrease in the light sensed by the phototransistor [4]. This fluctuation reflected in the output current of the phototransistor is converted to frequency by a wide range linear V/F converter [5].

The amplification and digital conversion of the signal is made in one step by the V/F precision converter (integrated circuit LM331N). This circuit has a linear range of conversion from 1 Hz to 100 KHz, offering a great sensibility only limited by the associated microprocessor sample rate. (The V/F converter circuit is an adaptation of the LM231N typical application DS005680-9 National Semiconductor)

The digitalized signal is acquired and mathematically analyzed by a central processor unit implemented by a PIC16F84A-20. This microcontroller is programmed with a derivative/integrative algorithm (described later) capable of translating light fluctuations into locomotor activity counts.

The locomotor activity counter is then transmitted to a Personal Computer (PC) every a fixed, user-defined lapse of time, for data saving. This transmission is made through a serial interface with a RS-232 protocol.

The microcontroller also turns on/off the infrared leds when the acquisition starts.

Figure 4:
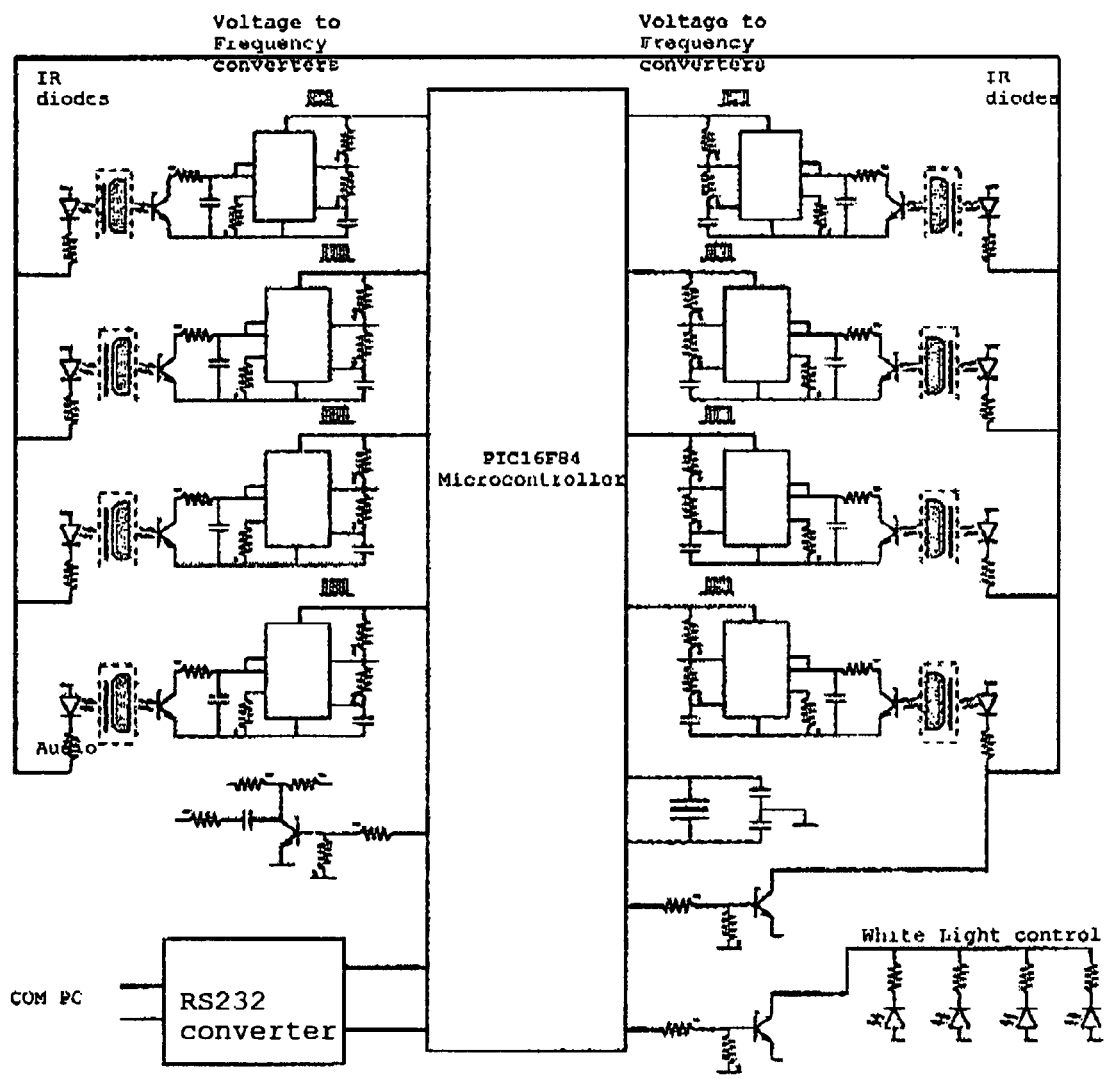
FIG. 4: Electronic circuit diagram of an eight-channel board for reading that comprises the acquiring device of FIG. 1.

The acquisition block described in FIG. 1 is repeated for each of the 96 wells [3]. This block is materialized by the electronic circuit shown in FIG. 4. The whole acquisition system is composed of 6 acquisition boards, 8 channels each, totalizing 48 channels per register allocation unit. One 96 microtiter plate is placed into one allocation unit.

The acquisition board (schematized in FIG. 4) contains 8 V/F converters [5], 1 microprocessor [6] and associated components.

As an accessory four white LEDS may be added that work intermittently during 24 hour periods and with 50% load cycles to use biological rhythm systems, when it is necessary or convenient to synchronize the animals with daily light-darkness cycles.

The input/output pinout of the microcontroller [6] is:
1.—8 inputs assigned to read V/F converters [4].
1.—1 output to control 8 infrared LEDs.
1.—1 output to control illumination LEDs.
1.—1 output assigned to repeat the read frequency of V/F converters (used for calibration of the system).
1.—2 input/outputs for Serial communication.

Each acquisition board has an address number assigned to the microcontroller. This address number is used for PC communication.

Infrared LEDs [1] are activated for 30 sec. After this acquisition time the microcontroller [6] waits for PC communication. Digital processing multiplexes 4 channels each acquisition cycle due to processing speed limitation (using the faster PI16C622-40 MHz microcontroller this multiplexing is not required).

The PC collects the data every 30 seconds, after which the acquisition cycle starts over. This time lapse provides 1 sample/minute, which is an acceptable timing interval for chronobiological and other studies. This time could be adjusted, from few seconds to minutes, obtaining similar results.

Description of the mathematical signal processing:

The algorithm to process the digital signal consists of:

1) Calculation of the period between 2 peaks of the square frequency wave:

The number of sample cycles is counted between one upward peak flank and the next. Since sample speed is programmed to 10 Kbauds/second, maximum frequency to resolve is 5 KHz. To avoid problems for undersampling, the basal frequency of the converters is adjusted to 3 KHz, by adjusting the power of the IR LEDs with resistors.

2) the Derivation of the period (n) is calculated according to the following equation:

$$\text{Derivative}(n) = \text{Period}(n) - \text{Period}(n-1)$$

3) the integration of the derivatives is calculated as follows:

$$\text{Integral}(n) = \text{Integral}(n-1) + \text{Derivative}(n)$$

This processing is equivalent to the calculation of a FIR DC blocker filter with an R value of 1. It is used to remove the basal signal value.

4) If the Integral Value is greater than a threshold (calculated empirically as the 6% of the previous Period) then the locomotor activity is recognized:

$$\text{IF ABS(Integral)} > 0.06 * \text{Period}(n-1) \rightarrow \text{OK Activity \& Integral} = 0$$

(ABS=Absolute value)

When the locomotor activity is detected an activity counter is incremented. This counter value is then transmitted to the PC when required.

The communication between the microcontroller and the PC is performed by the RS-232 interphase (COM port or USB adapter). The data is then collected by dedicated software with the following characteristics:
1.—Data saving of locomotor activity counter to text file (.txt) including date and time.

1.—Configuration of number of channels, sample time and communication port.
1.—Light turn on/off event programming.
1.—Calibration mode: manual activation of illumination, IR LEDs, real time mode (reading of the frequency of the V/F converter) for each channel.

Figure 5:
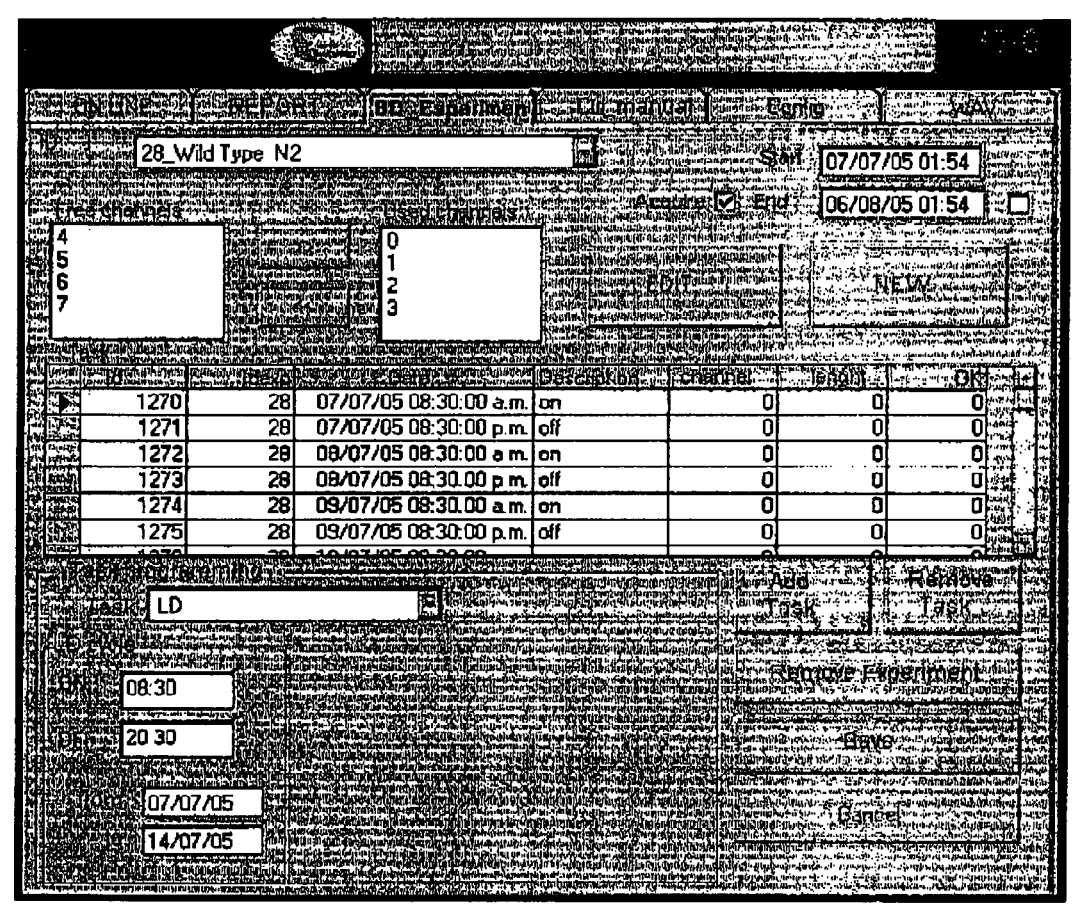

Once the data of the experiment is collected, the data could be plotted and analyzed with other software (i.e.: TEMPS or CLOCKLAB) locally or through a network connection to the PC (FIG. 5 represents the collected data). The acquisition program is not used for actogram plotting to avoid interference with the data collection timing.

Figure 6:
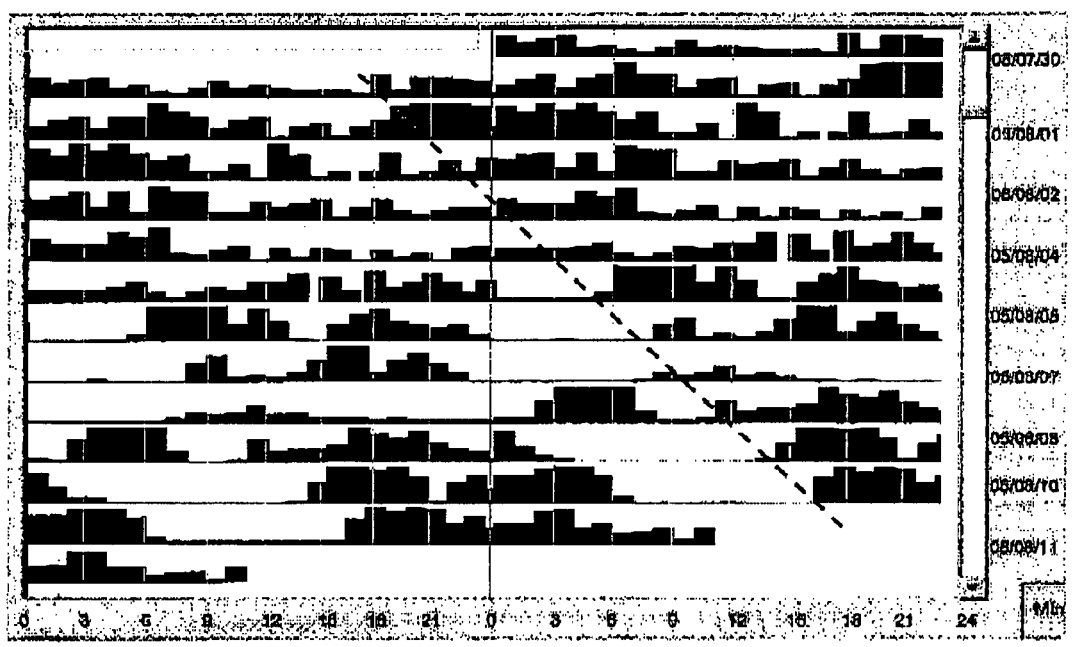
FIG. 6: Actogram of a wild type male nematode under constant darkness conditions. The black bars correspond to periods of activity of the nematode shown as a function of time, days are shown one under the other. The red line represents linear regression of the activity start.

FIG. 6 shows an example of an actogram plotted with data acquired with the described system. It is then possible to analyze the moment of higher activity, locomotor abnormalities, circadian period and also if the nematode is alive or not.

Thus, while the preferred features of the present invention have been described as to enable one skilled in the art to construct and use the apparatus and method of the present invention, it is understood that variations and modifications may be employed without departing from the main intent of the present invention, as defined in the following claims. Accordingly, the proceeding description is intended to be exemplary and should not be used to limit the scope of the invention. The scope and the invention should be determined only by reference to the following claims.

The invention claimed is:

1. A method for tracking locomotor activity of nematodes or similarly sized small organisms, characterized by comprising the following steps:
   isolating a plurality of organisms to be recorded in a plurality of individual closed habitats, generally placing one organism per habitat;
   traversing each isolated habitat with a microbeam with the appropriate characteristics to produce a measurable diffraction with the organism's body without altering the behavior or physiology of the organism, previously filtering each microbeam through microtransparencies preceding the closed habitats;
   detecting the intensity or the power of the microbeam crossing the closed habitat;
   determining whether there is fluctuation or attenuation in the measured microbeam intensity or power caused by the diffraction of the organism body crossing the microbeam, according to a detection threshold, and recording the locomotor activity of the organism, located inside the habitat, based on the determination of fluctuations of the determined microbeam parameters.

2. The method of claim 1, characterized in that the closed habitats contain an axenic medium, with a low optical absorbance in the optical range of the microbeam wavelength.

3. The method of claim 1, characterized by an infrared microbeam.

4. The method of claim 3, characterized in that the microbeam has a wavelength of around 940 nm.

5. The method of claim 1, characterized by irradiating the microbeams into the closed habitats at a power of less than 1 mW/cm$^2$.

6. The method of claim 1, characterized in that the microbeams are irradiated in alternating on/off duty cycles.

7. The method of claim 6, characterized in that each ON cycle lasts about half a minute.

8. The method of claim 1, characterized in that the microtransparent filters are formed by microholes of around 100 μm diameter in a dark plate.

9. The method of claim 1, characterized by a detection system which includes the conversion of the measured signal to a frequency directly proportional to the incident light.

10. The method of claim 1, characterized in that the steps of detecting fluctuation or attenuation in the measured microbeam intensity or power and recording the locomotor activity of the organism include:
    calculating the period between two successive peaks of the frequency wave,
    calculating the derivative of the period,
    integrating successive derivates and
    generating an activity register every time the integration value passes a threshold precalculated as a function of the previous period.

11. The method of claim 10, characterized in that said threshold is precalculated as 6% of the previous frequency period.

12. The method of claim 1, characterized in that said detection of the fluctuation in the measured intensity or power comprises detecting small and transient decreases in the intensity or the power of the measured microbeam.

13. The method of claim 1, characterized by the additional steps of entraining the organisms to daily light-and-dark cycles and analyzing whether said fluctuations follow a circadian pattern.

14. A behavioral record obtained by the method of one of claim 1.

15. The method of claims 1, wherein the method is performed to produce one of screening of mutants, toxicity of compounds, and pharmacological tests.

16. An apparatus for measuring locomotor activity of nematodes or similarly sized small organisms, comprising:
    a plate comprising a plurality of closed habitats, each suitable for cultivating one of said organisms,
    a plurality of respective infrared microbeam generator means, each having an output provided with a microhole or microtransparency and aligned through a corresponding closed habitat;
    a plurality of respective infrared microbeam receiver means, each aligned with a corresponding generator output such that each habitat is located in between a respective pair of generator and receiver means, in order for each receiver means to produce an output signal proportional to the received intensity or power of an infrared microbeam;
    receiver circuit means for detecting fluctuations in the output signal; and
    a register linked to the output of the fluctuation detector circuit means for registering the locomotor activity of the organism based on the fluctuations detected in the microbeam intensity or power.

17. The apparatus of claim 16, characterized in that each habitat contains an axenic medium with low infrared optical absorbance.

18. The apparatus of claim 16, characterized in that said microbeam generator means output power at less than 1 mW/cm$^2$.

19. The apparatus of claim 16, characterized in that the fluctuation, detector means includes a V/f converter.

20. The apparatus of claim 19, characterized by including a processor circuit connected to the V/f converter output and containing derivation/integration algorithms.

21. The apparatus of claim 16, characterized by further including means for irradiating said habitats with daily light-dark cycles.

* * * * *